United States Patent [19]

Atwood et al.

[11] 4,053,236
[45] Oct. 11, 1977

[54] ABSORBANCE MEASURING PHOTOMETER

[75] Inventors: John G. Atwood; Hamilton W. Marshall, Jr.; Charles F. de Mey, II, all of Redding, Conn.

[73] Assignee: The Perkin-Elmer Corporation, Norwalk, Conn.

[21] Appl. No.: 703,520

[22] Filed: July 8, 1976

Related U.S. Application Data

[63] Continuation of Ser. No. 499,617, Aug. 22, 1974, abandoned.

[51] Int. Cl.$^2$ .............................................. G01J 3/50
[52] U.S. Cl. ................................. 356/189; 356/184; 356/206
[58] Field of Search .......... 356/81, 88, 94, 96, 356/97, 179, 180, 184, 195, 189, 201, 188, 204–206

[56] References Cited

U.S. PATENT DOCUMENTS

| | | |
|---|---|---|
| 2,577,814 | 12/1951 | Saunderson et al. ............ 356/81 |
| 2,879,393 | 3/1959 | Cary et al. ....................... 356/94 |
| 3,022,704 | 2/1962 | Cary ................................ 356/94 |
| 3,542,515 | 11/1970 | Scott ........................... 356/97 UX |
| 3,725,204 | 4/1973 | Marshall et al. ............ 356/97 UX |
| 3,737,234 | 6/1973 | Shibata et al. .................. 356/88 |
| 3,832,062 | 8/1974 | Van den Bosch ............... 356/97 |

Primary Examiner—F. L. Evans
Attorney, Agent, or Firm—S. A. Giarratana; F. L. Masselle; J. D. Crane

[57] ABSTRACT

An absorbance measuring photometer, for measuring the absorbance of a sample in a sample cell, in which light of preselected wavelengths from one of two alternately utilizable sources of different wavelengths is formed into a beam and the etendu of the beam defined. The beam is then split into two separate beams one of which is directed through the sample cell onto a first detector and the other of which is passed directly onto a reference detector. The beam is so directed though the sample cell that it does not touch the cell walls and both beams are imaged on their respective detectors so as to be wholly within the photosensitive area thereof.

11 Claims, 4 Drawing Figures

ABSORBANCE MEASURING PHOTOMETER

BACKGROUND OF THE INVENTION

This is a continuation application of Ser. No. 499,617, filed Aug. 22, 1974 now abandoned This invention relates to photometric apparatus in general and more particularly to an improved photometer particularly useful in measuring photoabsorbance of liquids.

In a copending application of John G. Atwood et al., Ser. No. 594,951 filed July 10, 1975 as a continuation of now abandoned application Ser. No. 499,602 of John G. Atwood et al. filed on Aug. 22, 1974, is disclosed a completely automated analysis apparatus for analyzing micro quantities of reacting mixtures made up of a diluted serum sample and two reagents.

It has been common practice in the prior art when designing sensitive and stable photometers for measuring small changes in absorbance of samples to achieve sensitivity and stability through the use of a double beam and optical modulation system in which a beam of spectrally filtered radiation or portions of the beam from a suitable source of selected wavelengths is alternately directed along a path through the sample and a reference path by passing the sample. The sample and reference beams are then combined on a single detector to produce a periodically time-varying signal. In these prior art systems, the periodic signal is then demodulated to generate a signal representing the difference in absorbance between the sample and reference paths. Such prior art apparatus has been able to measure, as a least detectable quantity, a quantity in absorbance of approximately $5 \times 10^{-4}$ absorbance units. Furthermore, most apparatus of this nature has operated with fairly large samples. It will be recognized that if small samples can be used, the quantities of reagents consumed in analysis can be reduced, thereby reducing the cost of testing.

Thus, it is the object of the present invention to provide a photometer with improved accuracy and which can measure absorbance in extremely small micro sized samples.

SUMMARY OF THE INVENTION

The photometer of the present invention is highly stable and has very high sensitivity detecting extremely small changes in absorbance in a fluid sample at a particular wavelength of interest. It also exhibits improved sensitivity of measurement of the rate of change of absorbance of a fluid sample over a short period of time, as is desired in kinetic analysis using reactions catalyzed by enzymes. Furthermore, the invention broadens the dynamic range of absorbance over which a small change in absorbance can be measured; all with small sample volumes, e.g. 100 microliters or less. The photometer of the present invention does not require the modulation (or "chopping") found in the prior art but still achieves a sensitivity which is an order of magnitude better than that found in prior art photometers, i.e., it can regularly measure changes as small as $5 \times 10^{-5}$ absorbance units in absorbance of fluid samples. The photometer achieves this result through a high stability optical design in an unmodulated double beam arrangement. To this end, the invention contemplates a photometer in which light from a source producing preselected wavelengths is formed into a beam and the etendu of the beam defined. The beam is then split into two separate beams one of which is directed through the sample cell in such a manner that it does not touch the cell walls. Both beams are imaged on respective detectors so as to be wholly within the photosensitive areas thereof.

In addition, the sample cell itself is thermally isolated within a cavity and maintained at a predetermined temperature. Because of its thermal isolation, the sample, which is preheated on its way through the photometer cell, and the cell remain at a constant temperature throughout the measurement cycle. The sample is heated by being passed through a thermostated metal block whose temperature is regulated by a control system including a thermistor and a heat pump.

DETAILED DESCRIPTION OF THE PREFERRED EMBODIMENT

Figure 1:
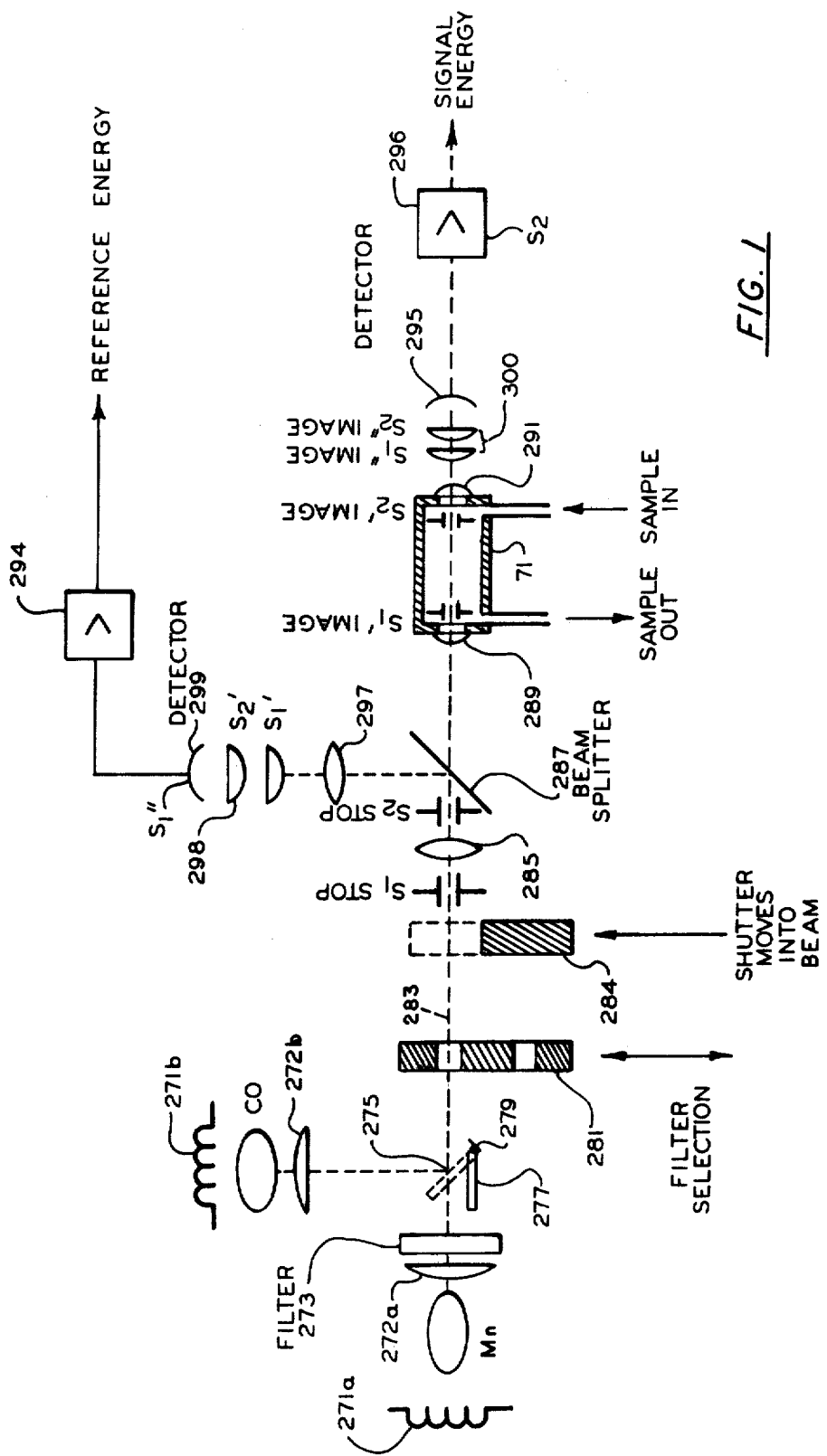
FIG. 1 is an optical mechanical schematic diagram of the photometer of the present invention.

Referring first to FIG. 1, the photometer comprises a light source capable of emitting light of two predetermined wavelength bands. In the illutrated embodiment, the source takes the form of two hollow cathode lamps: a manganese lamp 271a emitting light at about 404 nm and a cobalt lamp 271b emitting light at about 340 nm. Since the wavelengths emitted are those of the atoms of the lamps' cathode, these wavelengths are extremely stable and repeatable, contributing to the stability of the photometer. Lenses 272a and 272b are provided repectively in front of the lamps 271a and 271b to form beams of light. The two light path formed by lenses 272a and 272b intersect at a point 275 where a mirror 277 rotatable about an axis 279 is installed. Which of the lamps is used as the light source is determined by the test being run. Depending on the selection, a control signal will cause the mirror to be rotated to the position in solid lines for light at 404 nm or the position shown on dotted lines for light at 340 nm. In conjunction therewith, a movable filter 281 is positioned to pass only a frequency band containing the selected wavelength. The selected wavelength of light then travels along the optical axi 283 toward a photometer sample cell 71. It is important to define the etendu of the beam in order that a beam of known and controlled throughput of light flux be provided and so that it will be possible to split the beam into a signal path and a reference path, each of which will also have known and controlled throughputs of light flux. In so defining the etendu and in generating the beam, it is essential that the light source have an area of essentially uniform brightness and that the image of this area of uniform brightness overfill the first stop upon which it is imaged so that the full cross-section of the beam is of the same uniform brightness in spite of small mechanical motions of the source. The etendu is defined through the use of a field stop S1 and an aperture stop S2 with a lens 285 therebetween. The light beam prior to encountering the stops S1 and S2 passes a shutter 284, controlled by an appropriate timing singal; the shutter is normally maintained closed and is opened only for a predetermined period during which the aborbance measurement is made, for reasons described below. The beam having a defined etendu is then directed to a beamsplitter 287 of the coated type which preserves uniformity of illumination in both light paths. The beamsplitter 287 is coated so as to transmit approximately 90% of the beam and reflect the remaining 10%. Thus, the two beams formed thereby are of lower intensity than the original beam, but both are of uniform illumination across their respective cross-sections. The transmitted portion of the beam, i.e., the portion containing 90% of the energy, enters the cell 71, first passing through a lens 289. The lens 285 images the field stop S1 near the entrance to the cell, with the lens 289 imaging the stop S2 near the exit of the cell. These lens means are shown only as examples and it will be recognized by those skilled in the art that any equivalent lens arrangement which will so image the stops may be used. The purpose of this imaging is to insure that the light path is kept away from the sides of the cell, and further that the boundaries of the beam are well defined, so that small mechanical motions of the parts may occur without the beams hitting either the walls of the cell, or the margins of any of the optical parts. This makes the throughput of light flux in the beam stable with respect to small mechanical or optical disturbances. A further lens 291 is provided at the exit end of the cell 71. This lens images the stop S1 at a condenser lens arrangement 300. The condenser lenses shown as two lenses image the stop S2 on a detector 295. It is essential that these lenses be able to encompass a large input angle as large as possible so that they can collect a maximum of scattered light. Although the beam is well defined travelling through the cell 71, the liquid therein may scatter the beam to some degree and the improved results obtained with the photometer system are at least partially due to this ability to collect nearly all such scattered lights. Furthermore, it is essential that the lenses 300 image the light well within the boundaries of the active area of the detector 295 so that all of the output from the cell is measured in spite of small mechanical motions of the optical parts which cause the beam to move.

Light in the reflective path from beamsplitter 287 is directed through a lens 297 and a pair of condenser lenses 298. Lens 297 images the field stop $S_1$ and $S_1'$ on the first lens and the stop $S_2$ at $S_1'$ on the second lens. The second lens images the image $S_1'$ and $S_1''$ on a second detector 299. Again, it is essential that all of the beam be imaged within the sensitive area of the detector 299.

As will become more evident below, the output of the detector 299, which i a reference detector, is used to cancel from the output of the detector 295, which is the signal detector, any output variations resulting from variations at the illumination sources 271a and 271b. Any variations occurring before the splitting of the beam at 287 will thus be cancelled out. The signals from the detectors as illustrated are amplified in repective amplifiers 296 and 294 and then processed in a manner to be decribed below. The shutter 284 is kept closed, i.e., in a position to block optical path 283, except during a measurement cycle, i.e., when samples are being transferred the shutter remains closed. This prevents any inaccuracies due a response time effect of the detectors 295 and 299 by causing light from both reference and sample beams to be applied to the respective detectors at the same time. Were the shutter left open, the light of the reference beam would be on the reference detector 299 continuously whereas, the detectors 295 could have a lag in responding to a sample transferred to the cell. Under such circumstances, errors could result because of the difference in the history of illumination on the two detectors.

If these teachings are faithfully carried out, then the only phenomena that will significantly affect the ratio of the signals detected in the two beams is a change in absorbance of the sample.

In spite of all precaution, small mechanical and optical disturbances will occur, some of which may cause the images to move or change size on the detectors' sensitive areas. Therefore, it is advantageous that the detectors have uniform response to light over their active area.

Figure 2:
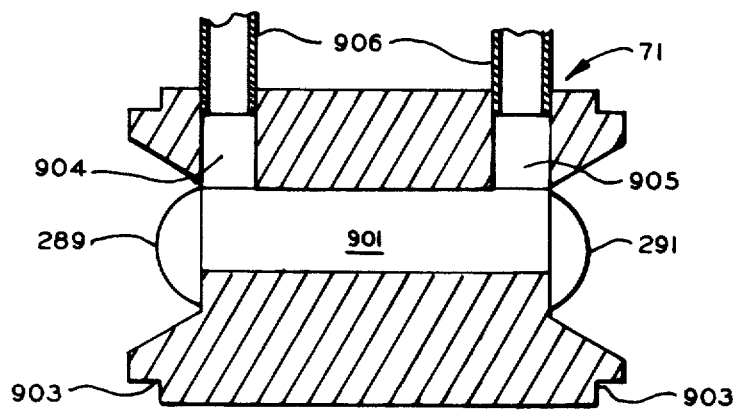
FIG. 2 is a more detailed cross-section of the sample cell of FIG. 1.
Figure 3:
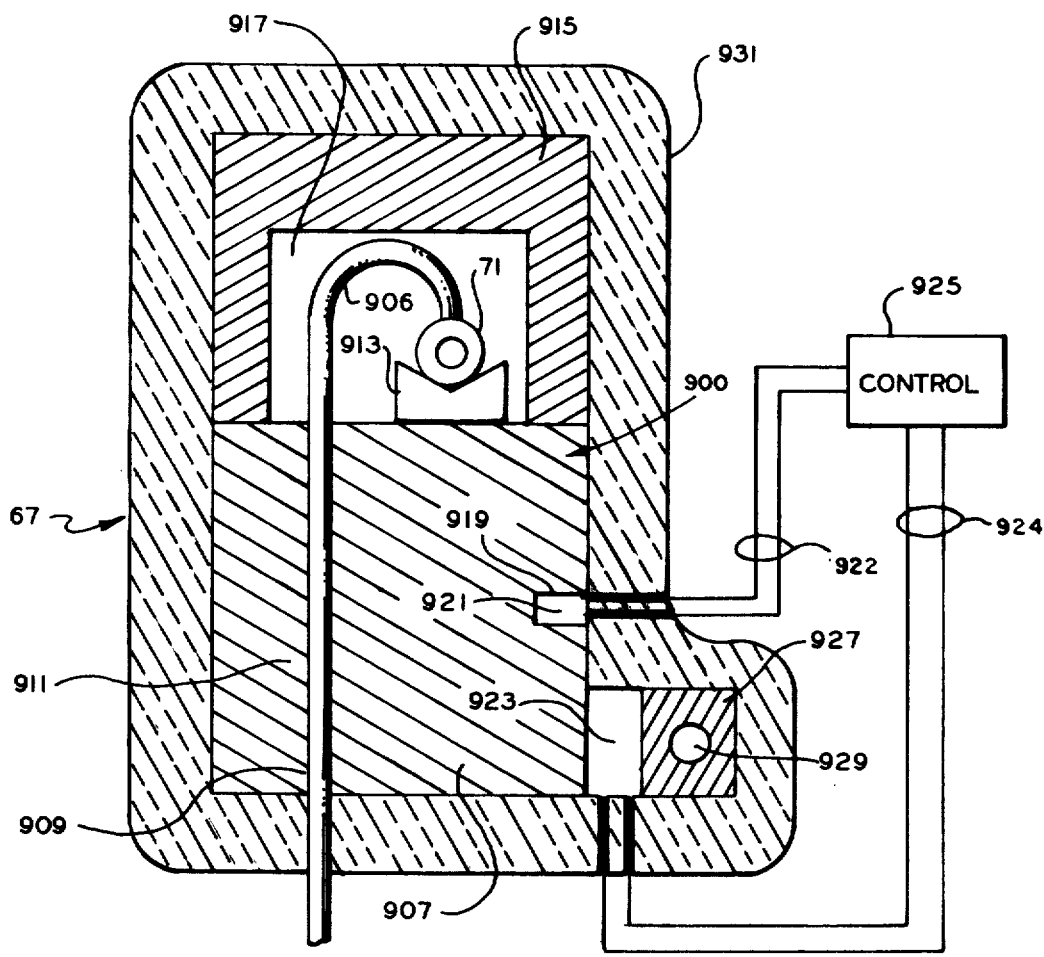
FIG. 3 is a cross-sectional view of means which may be used to control temperature.

Further, since the response of detectors to light is dependent upon their temperature, it is important that the two detectors be at the same temperature and that this temperature not change during the measurement. A more detailed drawing of the photometer cell 71 is shown on FIG. 2. The cell itself is made of silver and defines a sight passage 901 in which the sample rests during analysis. The ends of passage 901 ae closed by lens-shaped members 289 and 291 which form part of the optical system as already explained. Cell 71 is essentially cylindrical in its external configuration and is provided with cutouts 903 for resting the cell in a plastic block as will be described presently. Openings 904 and 905 are provided in the cell 71 in flow communication with the respective ends of passage 901, enabling the introduction and removal of a reaction sample. The transfer of a reaction sample to cell 71 may be effected by means of a transfer system described and claimed in a copending application of John G. Atwood et al. for U.S. Let. Pat. Ser. No. 499,618, filed Aug. 22, 1974, and assigned to the same assignee as the present invention. Inserted into each of the openings 904 and 905 is a stainless steel nipple 906. While it is important that the sample be maintained at a particular temperature during measurement, it is more important that the temperature remain constant during analysis. For example, it may be sufficient if the temperature of the sample in the cell is within 0.2° C of the desired temperature, 30° C, for a particular enzyme determination; however, the temperature during the analysis period should not vary more than 0.01° C. FIG. 3 shows a heat exchanger assembly 900 for bringing the sample to a desired temperature and maintaining it at that temperature. The assembly comprises a thermostated base block 907 made of aluminum and containing a tubular passage 909 within which is inserted a stainless tube 911. The upper end of tube 911 is connected through Tygon tubing to the sample cell nipple 906 at the inlet end of sight passage 901. Cell 71 rests on a plastic V block 913, having good thermal insulation properties, located on top of the block 907. A cover 915, also of aluminum, is placed over the block 907 and bolted in place.

A recess 919 in block 907 accommodates the insertion of a thermistor 921. Attached to the side of block 907 below thermistor 921 is a heat pump 923 which preferably takes the form of a Peltier device such as Borg Warner Part No. 930–17. Leads 922 from thermistor 921 connected to a control device 925 which provides outputs over leads 924 to operate the heat pump 923 in conventional fashion. On the opposite side of heat pump 923 with respect to block 907 is a further metal block 927 having a passage 929 through which water is circulated to remove heat from the heat pump when it is operating in a cooling mode. The entire assembly is surrounded with insulation. In operation, heat pump 923 adjusts the temperature of the aluminum block 907 to the desired value. This results in the temperature of cavity 917 being approximately at the desired value, i.e., is close enough to this value to provide accurate results. However, as noted above, the sample must not change its temperature during measurement. The use of the silver cell and its thermal isolation from block 907 by means of the Tygon tube connection between tube 911 and nipple 906, as well as the plastic V block 913, assures the requisite temperature invariance. The high thermal conductivity of the silver causes it to reach an equilibrium temperature with the sample very quickly. Heat pump 923 proportionally changes the temperature of the aluminum block slightly, e.g., as the temperature of the block drops a small amount, the heat pump will increase its heat flow to bring it up to the set value. The block temperature does not vary much but even a small variation would be sufficient to affect the accuracy of the photometric analysis of experienced at the sample cell. The detectors, which are located within the recess 919 will also be maintained at essentially constant temperature.

Figure 4:
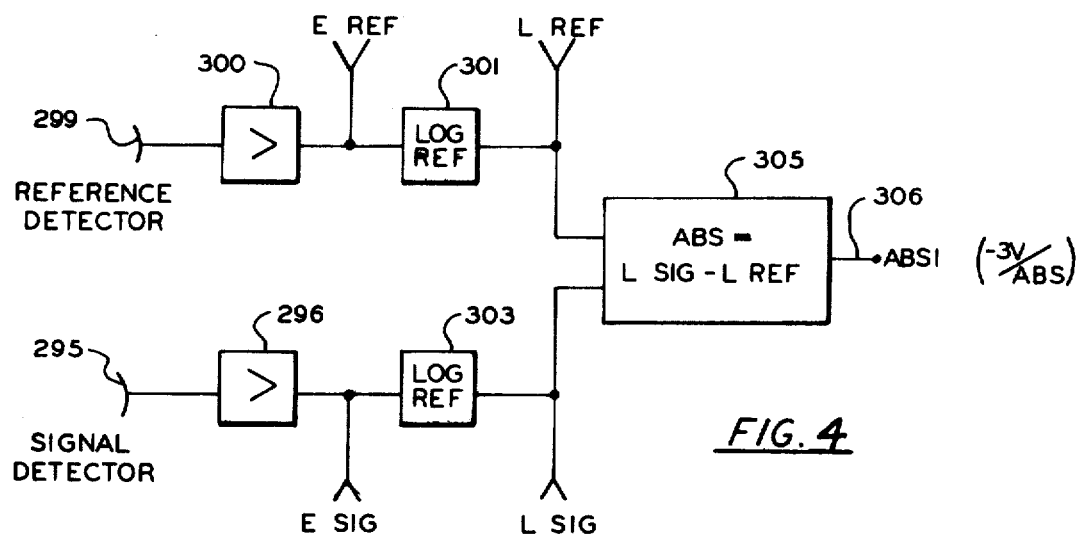
FIG. 4 is a block diagram of the detector and amplifier circuit of the present invention.

A basic block diagram of the detector and preamplifier arrangement for the photometer is shown on FIG. 4. Detectors 299 and 295 are used along with amplifier stages 300 and 296. The amplifiers respectively are provided with test point outputs indicated "E ref" and "E sig". These outputs are also provided into a logarithmic circuit, the longarithmic circuits being designated 301 and 303. Circuit 301 takes the log of the reference detector output and circuit 303 the log of the signal. These two logarithmic signals are also provided as outputs to test points designated L ref and L sig. From these two values, the absorbance is calculated by subtracting in an analog subtractor 305 the logarithm of the reference signal from the logarithm of the measurement signal. The output then is provided on a line 306. A preferred circuit for use with the photometer of the present invention is that diclosed and claimed in a copending application of John G. Atwood et al., Ser. No. 499,855 filed on Aug. 22, 1974, now U.S. Pat. No. 4,014,612 and assigned to the same assignee as the present invention.

Thus, an improved photometer for use in automatic analysis has been shown. Although a specific embodiment has been illustrated and described, it will be obvious to those skilled in the art that various modifications may be made without departing from the spirit of the invention which is intended to be limited solely by the appended claims.

What we claim is:

1. A method of measuring the photo-absorbance of a translucent reaction mixture comprising:
   a. placing the reaction mixture in a sample cell
   b. forming a first beam of light containing predetermined wavelengths;
   c. defining the etendu of said first beam with a field stop and aperture stop;
   d. splitting said first beam into second and third contemporaneous beams while preserving uniformity of illumination over both said second and third beams;
   e. passing said second beam through said sample cell so as to symmetrically image said field stop near the entrance of said cell and said aperture stop near the exit of said cell, both said images being located so that said second beam does not touch the walls of said cell;
   f. forming an image of said aperture stop wholly within the sensitive area of a first detector using large angle optical means to capture a major portion of light scattered by the reaction mixture in the cell;
   g. imaging one of said field and aperture stops in said third beam wholly within the sensitive area of a second detector; and
   h. using the output of said second detector to cancel out any flucutations in the output of said first detector resulting from changing brightness in said first beam of light.

2. The method of claim 1 including the further step of occluding said light beams until the reaction mixture is in the sample cell whereby neither of said first and second detectors is exposed to the light beams prior to making the absorbance measurement.

3. The method of claim 1 including the further step of maintaining said detectors at substantially equal and constant temperatures.

4. Apparatus for measuring the absorbance of a reaction mixture in a photometer sample cell comprising:
   a. a light source emitting predetermined wavelengths;
   b. means for forming the light from said source into a first beam;
   c. means for defining the etendu of said first beam including a field stop and an aperture stop;
   d. means for splitting said first beam into second and third contemporaneous beams while preserving the uniformity of illumination over both second and third beams and directing said second beam through said cell;
   e. lens means to symmetrically image said field stop near the entrance of said cell and said aperture stop near the exit of said cell in such manner that, when passing through said cell, said second beam does not touch the sides thereof;
   f. a first detector;
   g. means forming an image of said aperture stop wholly on the sensitive area of said first detector;
   h. a second detector in the path of said third beam;
   i. means forming an image of one of said field and aperture stops wholly on the sensitive area of said second detector; and
   j. signal amplifying means including means to cause the signal from said second detector to cancel out any variations in the signal from said first detector resulting from light source fluctuations.

5. Apparatus according to claim 4 further including light occluding means displaceably interposed in said first beam.

6. Apparatus according to claim 5 further including a filter interposed in said first beam passing only a selected band of said wavelengths.

7. Apparatus according to claim 6 further including:
   a. another light source emitting different wavelengths;
   b. a switchable mirror for directing light from either said one or other light source to said sample cell;
   c. a second filter adapted to pass light in another band of wavelengths; and
   d. means to selectively position one and the other of said filters in the light path of said first beam.

8. Apparatus according to claim 4 further including means for maintaining said detectors at substantially equal and constant temperatures.

9. The method of claim 1 wherein said first beam i split so that said second beam has substantially greater energy than said third beam.

10. Apparatus according to claim 4 wherein said means for splitting said first beam includes means for dividing the energy between said second and third beams so that said second beam contains about 90% of the energy and said third beam contains about 10% thereof.

11. Apparatus according to claim 4 further comprising means for passing said third beam, from said means for splitting said first beam, to said second detector without passing through a cell means.

* * * * *